United States Patent
At et al.

(10) Patent No.: US 8,614,199 B2
(45) Date of Patent: Dec. 24, 2013

(54) COMPOSITIONS COMPRISING AT LEAST ONE COMPLEX COMPOSED OF A DERIVATIVE OF NAPHTHOIC ACID AND OF AT LEAST ONE CYCLODEXTRIN AND USES THEREOF

(75) Inventors: Emmanuelle At, Antibes (FR); Claire Mallard, Mougins (FR)

(73) Assignee: Galderma Research & Development, Biot (FR)

( * ) Notice: Subject to any disclaimer, the term of this patent is extended or adjusted under 35 U.S.C. 154(b) by 56 days.

(21) Appl. No.: 13/262,498

(22) PCT Filed: Apr. 9, 2010

(86) PCT No.: PCT/FR2010/050681
§ 371 (c)(1),
(2), (4) Date: Dec. 27, 2011

(87) PCT Pub. No.: WO2010/116098
PCT Pub. Date: Oct. 14, 2010

(65) Prior Publication Data
US 2012/0094954 A1      Apr. 19, 2012

(30) Foreign Application Priority Data
Apr. 9, 2009   (FR) .................................... 0952336

(51) Int. Cl.
*A61K 31/715*   (2006.01)
*A61K 31/07*   (2006.01)

(52) U.S. Cl.
USPC ............................................ 514/58; 514/725

(58) Field of Classification Search
USPC .................................................. 514/58, 725
See application file for complete search history.

(56) References Cited

U.S. PATENT DOCUMENTS

| 2006/0246140 A1 | 11/2006 | Lochard et al. |
| 2008/0008727 A1 | 1/2008 | Fredon et al. |
| 2008/0253986 A1 * | 10/2008 | Mallard et al. ............. 424/78.37 |

FOREIGN PATENT DOCUMENTS

| WO | WO 2004/096284 A1 | 11/2004 |
| WO | WO 2006/070093 A1 | 7/2006 |

OTHER PUBLICATIONS

International Search Report (PCT/ISA/210) issued on Aug. 10, 2010, by European Patent Office as the International Searching Authority for International Application No. PCT/FR2010/050681.

* cited by examiner

Primary Examiner — Elli Peselev
(74) Attorney, Agent, or Firm — Dentons US LLP

(57) ABSTRACT

A composition is described for topical application comprising, in a physiologically acceptable medium, at least one complex composed of a naphthoic acid derivative of formula (I), salts and esters thereof:

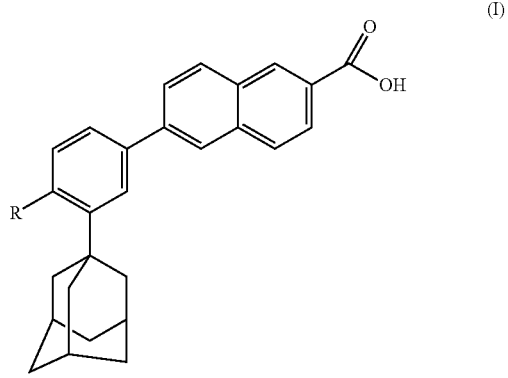

and of at least one cyclodextrin, said soluble molecular complex obtained by the technology of dense fluids under pressure.

16 Claims, 1 Drawing Sheet

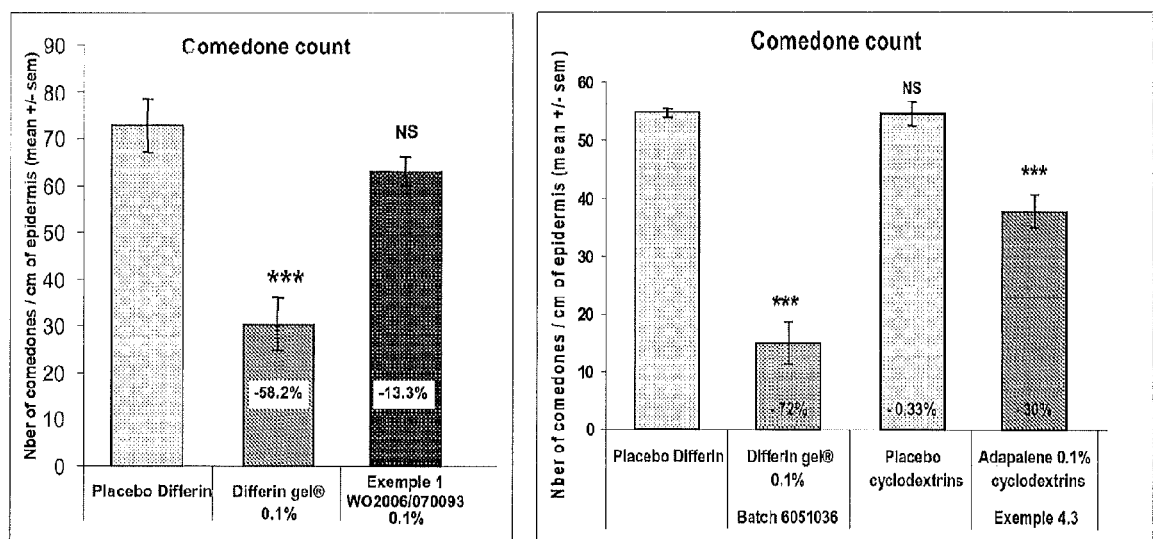

COMPOSITIONS COMPRISING AT LEAST ONE COMPLEX COMPOSED OF A DERIVATIVE OF NAPHTHOIC ACID AND OF AT LEAST ONE CYCLODEXTRIN AND USES THEREOF

This application is the United States national phase of PCT/FR2010/050681, filed Apr. 9, 2010, and designating the United States (published in the French language on Oct. 14, 2010, as WO 2010/116098 A1; the title and abstract were also published in English), which claims priority under 35 U.S.C. §119 of FR 0952336, filed Apr. 9, 2009, each earlier application hereby expressly incorporated by reference in its entirety and each assigned to the assignee hereof.

The present invention relates to compositions for topical application and to the uses thereof as cosmetic or pharmaceutical products, said compositions being intended in particular for treating acne.

Acne is a common multi-factor pathology that attacks skin rich in sebaceous glands (face, shoulder area, arms and intertriginous areas). It is the most commonly occurring form of dermatosis. The following five pathogenic factors play a determining role in the formation of acne:
1. genetic predisposition;
2. overproduction of sebum (seborrhoea);
3. androgens;
4. follicular keratinization disorders (comedogenesis); and
5. bacterial colonization and inflammatory factors.

There are several forms of acne, the common factor of all of them being attack of the pilosebaceous follicles. Mention may in particular be made of acne conglobata, acne keloid on the nape of the neck, acne medicamentosa, recurrent miliary acne, acne necrotica, acne neonatorum, premenstrual acne, occupational acne, acne rosacea, senile acne, solar acne and acne vulgaris.

Acne vulgaris, also known as polymorphous juvenile acne, is the most common. It comprises four stages:
Stage 1 corresponds to comedonal acne, characterized by a large number of open and/or closed comedones and of microcysts.
Stage 2, or papulopustular acne, is of mild to moderate seriousness. It is characterized by the presence of open and/or closed comedones and microcysts, but also of red papules and of pustules. It mainly affects the face and leaves few scars.
Stage 3, or papulocomedonal acne, is more serious and extends to the back, the thorax and the shoulders. It is accompanied by a larger number of scars.
Stage 4, or nodulocystic acne, is accompanied by numerous scars. It exhibits nodules and also has large painful purplish pustules.

The various forms of acne described above can be treated with active agents, such as antiseborrhoeics and antiinfectives, for example benzoyl peroxide (in particular, the product Eclaran® sold by the company Pierre Fabre), with retinoids, such as tretinoin (in particular, the product Retacnyl® sold by the company Galderma) or isotretinoin (the product Roaccutane® sold by Laboratoires Roche), or with naphthoic acid derivatives. Naphthoic acid derivatives, such as, in particular, 6-[3-(1-adamantyl)-4-methoxyphenyl]-2-naphthoic acid, commonly known as adapalene (the product Differine® sold by the company Galderma), are widely described and recognized as active ingredients which are as effective as tretinoin in the treatment of acne.

Adapalene in particular has a unanimously proved efficacy; however, it would be advantageous and useful for its topical tolerance, although higher than those of its competitors belonging to the same chemical class (tretinoin, tazarotene), to be improved.

The adapalene currently contained in formulations of gel or cream type is in dispersed form. Indeed, the various components present in the composition of the gel or cream do not make it possible to dissolve adapalene to a content of 0.1% and 0.3% (w/w). It is therefore necessary to introduce compounds into the composition that make it possible to dissolve adapalene.

The Applicant has succeeded in formulating adapalene in the form of cyclodextrin-based complexes that make it possible to dissolve this active principle in a formulation. The adapalene/cyclodextrin complex is obtained first by the technique of dense fluids under pressure and in particular of supercritical $CO_2$. This technique is based on the solvating power of $CO_2$ which can be adjusted as a function of the pressure and temperature conditions and the technical principle of which is described in patent application WO 2004/096284.

Once the adapalene/cyclodextrin complex is obtained in powder form, it is necessary to succeed in stabilizing this complex in solution. Indeed, once in water, the adapalene/cyclodextrin complex rapidly decomplexes and a precipitation of adapalene is observed.

The major problem to be solved is therefore to find a formulation where the dissolved complex will be stabilized. Indeed, the major criteria which leads to the selection of formulations is the decomplexation of adapalene, which should take place on the skin and not in the formulation.

In order to solve the technical problem, the Applicant has developed solutions necessary for the stabilization of the complex once in solution, but also for formulating galenic forms, such as gels in order to obtain an adapalene content of 0.1% or 0.3% (w/w) in which the adapalene/cyclodextrin complex remains physically and chemically stable.

Once the adapalene/cyclodextrin complex used is in a dissolved form in a formulation, the examples show an effect as regards the kinetics and therefore an improvement in the penetration of such a complex, and also a beneficial effect on the comedolytic activity.

Topically, pharmaceutical applications of cyclodextrins are significantly less common (Glymesason®), or even non-existent within the context of acne treatment.

The use of cyclodextrins with retinoids has already been described with the main objectives of increasing the solubility and the photostability in particular of retinol. Few articles or patents mention the use of cyclodextrins with the objective of improving the skin penetration and also the comedolytic activity linked to acne.

Application WO 2006/070093 describes a composition comprising adapalene dissolved in an aqueous medium with cyclodextrins and therefore comprises the physical mixing of adapalene and cyclodextrin in an aqueous medium without the solvating power of a dense fluid under pressure.

Thus, the present invention differs from the prior art in the sense that it consists in formulating adapalene in the form of cyclodextrin-based complexes that make it possible to dissolve this active principle in a formulation containing 0.1 and 0.3% (w/w) of adapalene. Adapalene is complexed by cyclodextrin without a salification step, the acid function of adapalene is here retained.

One subject of the present invention is therefore a composition, in particular a pharmaceutical composition and preferably a dermatological composition, intended in particular for topical application, comprising, in a physiologically acceptable medium, at least one complex formed with at least one compound derived from naphthoic acid of formula (I) below, salts and esters thereof, and a cyclodextrin or derivatives thereof.

Preferably, said composition does not comprise any depigmenting agent.

In particular, said composition does not comprise any depigmenting agent separate from the compound derived from naphthoic acid, in particular adapalene.

The term "physiologically acceptable medium" means a medium that is compatible with the skin, mucous membranes and/or the integuments.

The compound derived from naphthoic acid according to the invention corresponds to the compound of formula (I), salts and esters thereof:

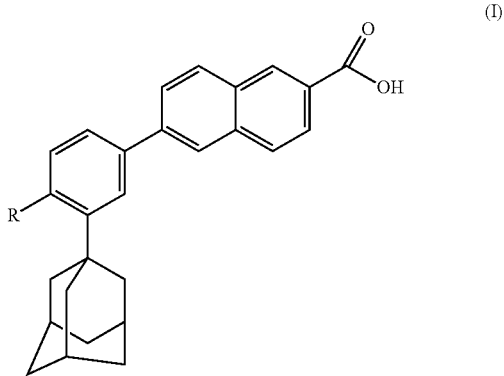

(I)

where R represents a hydrogen atom, a hydroxyl radical, a branched or unbranched alkyl radical having from 1 to 4 carbon atoms, an alkoxy radical having from 1 to 10 carbon atoms or a substituted or unsubstituted cycloaliphatic radical.

The term "linear or branched alkyl radical having from 1 to 4 carbon atoms" is intended to mean preferably methyl, ethyl, propyl and butyl radicals.

The term "alkoxy radical having from 1 to 10 carbon atoms" is intended to mean preferably methoxy, ethoxy, propoxy, butoxy, hexyloxy and decyloxy radicals.

The term "cycloaliphatic radical" is intended to mean preferably monocyclic or polycyclic radicals such as the 1-methylcyclohexyl radical or the 1-adamantyl radical.

The term "salts of naphthoic acid derivatives" is intended to mean salts formed with a pharmaceutically acceptable base, especially a mineral base such as sodium hydroxide, potassium hydroxide and aqueous ammonia or an organic base such as lysine, arginine and N-methylglucamine, but also the salts formed with fatty amines such as dioctylamine, aminomethyl propanol and stearylamine.

The term "esters of naphthoic acid derivatives" is intended to mean esters formed with pharmaceutically acceptable alcohols.

Preferably, among the naphthoic acid derivatives that may be included in the compositions according to the invention, 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid or 6-[3-(1-adamantyl)-4-hexyloxyphenyl]-2-naphthoic acid will be chosen.

More preferably still, the compound derived from naphthoic acid that can be used according to the invention is chosen from adapalene (6-[3-(1-adamantyl)-4-methoxyphenyl]-2-naphthoic acid), salts thereof and esters thereof.

The term "adapalene salts" is especially intended to mean the salts formed with a pharmaceutically acceptable base, especially mineral bases, such as sodium hydroxide, potassium hydroxide and aqueous ammonia or organic bases such as lysine, arginine and N-methylglucamine.

The term "adapalene salts" is also intended to mean the salts formed with fatty amines such as dioctylamine, aminomethyl propanol and stearylamine.

Preferably, the compound derived from naphthoic acid is adapalene.

In the compositions according to the invention, the concentration of the compound derived from naphthoic acid according to the general structure (I) mentioned above is between 0.001% and 10%, preferably between 0.01% and 5% and, more preferably, between 0.05% and 2% by weight of the total weight of the composition. Throughout the present text, unless otherwise specified, it is understood that, when concentration ranges are given, they include the upper and lower limits of said range.

Preferably, the concentration of compound derived from naphthoic acid is equal to 0.1%. Alternatively, the concentration of retinoid compound is preferably equal to 0.3%.

Cyclodextrins (CDs) are cyclic oligosaccharides constituted of ($\alpha$-1,4) $\alpha$-D-glucopyranose units with a lipophilic central cavity and a hydrophilic outer surface (Frömming K H, Szejtli J: "Cyclodextrins in pharmacy", Kluwer Academic Publishers, Dordrecht, 1994). Cyclodextrins are known to increase the solubility of molecules by forming a "cage"-shaped structure having an external hydrophilic part and an internal hydrophobic part. Cyclodextrins may thus form inclusion complexes with many medicaments by accepting the whole molecule, or more commonly the lipophilic part of the molecule, inside the cavity.

The most abundant natural cyclodextrins are $\alpha$-cyclodextrins, $\beta$-cyclodextrins and $\gamma$-cyclodextrins.

$\alpha$-Cyclodextrins (also known under the name Schardinger's $\alpha$-dextrin, cyclomaltohexaose, cyclohexaglucan, cyclohexaamylose, $\alpha$-CD, ACD, C6A) comprise 6 glucopyranose units. $\beta$-Cyclodextrins (also known under the name Schardinger's $\beta$-dextrin, cyclomaltoheptaose, cycloheptaglucan, cycloheptaamylose, $\beta$-CD, BCD, C7A) comprise 7 glucopyranose units and $\gamma$-cyclodextrins (also known under the name Schardinger's $\gamma$-dextrin, cyclomaltooctaose, cyclooctaglucan, cyclooctaamylose, $\gamma$-CD, GCD, C8A) comprise 8 glucopyranose units.

Among these three types of CDs, $\beta$-cyclodextrins appear to be the most useful complexing pharmaceutical agents due to the size of their cavity, their availability, their properties and their low cost.

According to Dr J. Szejtli ("Cyclodextrins", in Encyclopedia of Supramolecular Chemistry, Eds. Marcel Dekker, 2004) cyclodextrins are advantageous but also have limiting factors that restrict the application of cyclodextrins to certain types of pharmaceutical products. Furthermore, not all products are suitable for complexing with cyclodextrins. Many products cannot be complexed or else complexing does not provide any fundamental advantage. Inorganic compounds are generally unsuitable for complexing with cyclodextrins.

Cyclodextrin derivatives can also be used in the present invention. In cyclodextrins, each glucopyranose unit has three free hydroxyl groups that differ in their function and their reactivity.

The term "cyclodextrin derivative" is understood to mean a cyclodextrin of which all or some of the hydroxyl groups have been modified by substitution of the hydroxyl group or of the hydrogen atom.

Ester, ether, anhydro, deoxy-, acidic, basic, etc. derivatives may be prepared by chemical or enzymatic reactions well known to a person skilled in the art.

For example, in β-CDs, 21 hydroxyl groups may be modified by substituting the hydrogen atom or the hydroxyl group with a wide variety of groups such as alkyl, hydroxyalkyl, carboxyalkyl, amino, thio, tosyl, glucosyl, maltosyl, etc. groups.

Among preferred derivatives, mention may be made of the derivatives of α-cyclodextrins, β-cyclodextrins, γ-cyclodextrins and in particular the methyl derivatives of cyclodextrins such as TRIMEB (heptakis(2,3,6-trimethyl)-β-CD), DIMEB (heptakis(2,6-dimethyl)-β-CD) or else RAMEB (Randomly Methylated β-cyclodextrin); 2-hydroxypropyl-β-cyclodextrin (HPCD); 2-hydroxyethyl-β-cyclodextrin; 2-hydroxypropyl-γ-cyclodextrin and 2-hydroxyethyl-γ-cyclodextrin. Lastly, mention may also be made of cyclodextrins crosslinked with epichlorohydrin (EPC). In particular, mention may be made of the HPCD sold especially under the name Kleptose HPB® by Roquette and the RAMEB sold by Wacker.

Cyclodextrins are compounds that are widely used for responding to solubilization problems and they are particularly suitable for compounds that are not very soluble in water, such as adapalene (Didja et al.; Int. J. Pharm. 54 (1989), 175-179; Didja et al.; Int. J. Pharm. 111 (1994), 111-116; Loftsson et al.; Int. J. Pharm. 115 (1995), 255-258; Liu et al.; J. Pharm. Sci. Vol. 92 (12), 2003, 2449-2457).

Cyclodextrins are widely used for dissolving active principles that are not very soluble. The complexes most commonly encountered are based on steroids or on nonsteroidal anti-inflammatories with applications mainly orally, parenterally or ophtalmically.

Preferably, the cyclodextrins used are those of RAMEB (Randomly Methylated β-cyclodextrin) type.

According to one particularly preferred embodiment of the invention, the technique used to complex adapalene is the supercritical $CO_2$ technique. A technique based on the solvating power of $CO_2$, which can be adjusted as a function of the pressure and temperature conditions. The cyclodextrin used is a methyl-β-cyclodextrin. The complex, once prepared, is incorporated into a gel at a content of 0.1% w/w and 0.3% w/w of adapalene titre.

The compositions according to the present invention may be in any galenic form normally used for topical application, in particular in the form of aqueous, aqueous-alcoholic or oily dispersions, dispersions of lotion type, aqueous, anhydrous or lipophilic gels, emulsions of liquid or semi-liquid consistency of the milk type obtained by dispersing a fatty phase in an aqueous phase (O/W) or vice versa (W/O), or suspensions or emulsions of soft, semi-liquid or solid consistency of the cream, cream-gel, foam or ointment type or microemulsions, microcapsules, microparticles or vesicular dispersions of ionic and/or nonionic type, or else in the form of sprays.

Preferably, the compositions are in the form of a gel.

Those skilled in the art will take care to select the excipients constituting the compositions according to the invention according to the desired galenic form and such that the advantageous properties of the composition according to the invention are respected.

The composition according to the invention may also comprise one or more of the following ingredients:
a) one or more gelling agents;
b) one or more chelating agents;
c) one or more emollients; and
d) one or more preservatives.

By way of nonlimiting example of gelling agents and/or pH-independent gelling agents that may be included in the compositions according to the invention, mention may be made of the polymers of polyacrylic acid such as Carbopol 980NF, the acrylates/C10-30 alkyl acrylate crosspolymer sold under the name Pemulen TR-1 or Pemulen TR-2 by the company Noveon, the "electrolyte-insensitive" carbomers sold under the name Ultrez 20®, Ultrez 10®, Carbopol 1382® or Carbopol ETD2020NF® by the company Noveon, polysaccharides, nonlimiting examples of which include chitosans, xanthan gum such as Xantural 180® sold by the company Kelco, guar gum, cellulose and derivatives thereof such as the microcrystalline cellulose and sodium carboxymethyl cellulose sold under the name Avicel CL-611 by the company FMC Biopolymer, hydroxypropyl methyl cellulose, in particular the product sold under the name Methocel E4M premium by the company Dow Chemical, or hydroxyethyl cellulose, in particular the product sold under the name Natrosol HHX 250® by the company Aqualon, the family of magnesium aluminium silicates, such as the Veegum K sold by the company Vanderbilt, the family of acrylic polymers coupled to hydrophobic chains, such as the PEG 150/decyl/SMDI copolymer sold under the name Aculyn 44 (polycondensate comprising, as elements, at least one polyethylene glycol containing 150 or 180 mol of ethylene oxide, decyl alcohol and methylenebis(4-cyclohexylisocyanate) (SMDI), at 35% by weight in a mixture of propylene glycol (39%) and water (26%)), the family of modified starches such as the modified potato starch sold under the name Structure Solanace, or else mixtures thereof, and the gelling agents of the polyacrylamide family, such as the sodium acryloyldimethyltaurate copolymer/isohexadecane/polysorbate 80 mixture sold under the name Sepineo P 600® (or Simulgel 600 PHA®) by the company Seppic, the polyacrylamide/C13-14 isoparaffin/laureth-7 mixture, for instance that sold under the name Sepigel 305 by the company Seppic, the family of carrageenans, in particular divided up into four main families: κ, λ, β, ω, such as Viscarin® and Gelcarin® sold by the company IMCD.

As preferred gelling agent, mention may be made of the polymer of polyacrylic acid sold in particular under the name Carbopol 980NF® by Noveon.

Among the chelating agents, mention may be made, by way of nonlimiting examples, of ethylenediaminetetraacetic acid (EDTA), diethylenetriaminepentaacetic acid (DTPA), ethylenediaminebis(O-hydroxyphenylacetic acid) (EDDHA), hydroxy-2-ethylenediaminetriacetic acid (HEDTA), ethyldiaminebis(O-hydroxy-p-methylphenyl)acetic acid (EDDHMA) and ethylenediaminebis(5-carboxy-2-hydroxyphenyl)acetic acid (EDDCHA).

By way of preferred chelating agent, mention may be made of ethylenediaminetetraacetic acid (EDTA) sold in particular under the name Titriplex III®.

Among the humectants and/or emollients, the role of which is to hydrate the skin and to facilitate the application of the formulation, use is preferably made, without this list being limiting, of compounds such as glycerol, propylene glycol or propane-1,2-diol, dipropylene glycol, propylene glycol dipelargonate, lauroglycol, alone or as a mixture, sodium docusate, sorbitol, sugars (by way of example, glucose, lactose), PEGs (by way of example, Lutrol E400), urea or amino acids (by way of example, serine, citrulline, alanine).

By way of preferred humectant and/or emollient, mention may be made of glycerol, propylene glycol and sodium docusate.

Among the preservatives, mention may be made, by way of nonlimiting examples, of benzoic acid and its derivatives with benzyl alcohol, benzalkonium chloride, sodium benzoate, bronopol, chlorohexidine, chlorocresol and its derivatives, ethyl alcohol, phenethyl alcohol, phenoxyethanol, potassium sorbate, diazolidinyl urea, parabens such as propylparaben or methylparaben, taken alone or as mixtures.

By way of preferred preservative, mention may be made of parabens and phenoxyethanol or benzalkonium chloride, alone or as a mixture.

The composition according to the invention may also comprise one or more emulsifiers.

Emulsifiers are amphiphilic compounds which contain a hydrophobic portion with affinity for oil and a hydrophilic portion with affinity for water, thus creating a link between the two phases. Ionic or nonionic emulsifiers thus stabilize oil/water emulsions by becoming adsorbed at the interface and by forming lamellar liquid crystal layers.

The emulsifying power of nonionic emulsifiers is closely linked to the polarity of the molecule. This polarity is defined by the HLB (hydrophilic/lipophilic balance).

A high HLB indicates that the hydrophilic fraction is predominant and, conversely, a low HLB indicates that the lipophilic portion is predominant. For example, HLB values of greater than approximately 10 correspond to hydrophilic surfactants.

Emulsifiers may be classified, according to their structure, under the generic terms "ionic" (anionic, cationic or amphoteric) or "nonionic". Nonionic emulsifiers are emulsifiers that do not dissociate into ions in water and are therefore insensitive to variations in pH.

Mention may be made, as nonlimiting examples of nonionic emulsifiers exhibiting a high HLB, of sorbitan esters, such as POE(20) sorbitan monooleate, sold under the name of Tween 80® (HLB=15), or POE(20) sorbitan monostearate, sold under the name of Tween 60® (HLB=14.9), fatty alcohol ethers, such as POE(21) stearyl ether (HLB=15.5), sold under the name Brij 721® by the company Uniqema, or ceteareth-20, sold under the name Eumulgin B2® (HLB of 15.5) by the company Cognis, polyoxyethylene glycol esters, such as glyceryl stearate and PEG 100 stearate, sold under the name Arlacel 165 FL® (HLB=11) by the company Uniqema, or PEG 6 stearate and PEG 32 stearate, sold under the name Tefose 1500® (HLB=10) by the company Gatefossé, or sugar esters with a high HLB, such as PEG 20 methyl glucose sesquistearate, sold under the name glucamate SSE20® (HLB=15) by the company Amerchol, and sucrose laurate, sold under the name Surf hope C-1216® (HLB=16), and sucrose stearate, sold under the name Surfhope C-1811® (HLB=11) by the company Gattefossé. Preferably, said nonionic emulsifiers with a high HLB exhibit an HLB of between 10 and 18.

Mention will be made, as nonlimiting examples of nonionic emulsifiers exhibiting a low HLB (lipophilic emulsifiers), of sorbitan esters, such as sorbitan monostearate (HLB=4.7), sold under the name Span 60 by the company Uniqema, glycerol esters, such as glycerol monostearate, sold under the name Cutina GMSVPH (HLB=3.8) by the company Cognis, polyethylene glycol esters, such as PEG-6 isostearate, sold under the name Olepal Isostéarique® (HLB=8) by the company Gattefossé, or sugar esters with a low HLB, such as methyl glucose sesquistearate, sold under the name of Glucate SS® (HLB=6) by the company Amerchol, and sucrose dilaurate, sold under the name of Surfhope C 1205 (HLB=5), and sucrose tristearate, sold under the name of Surfhope C-1803® (HLB=3), by the company Gattefossé.

Mention may also be made, as other nonionic emulsifiers, of self-emulsifying waxes that make it possible to obtain stable emulsions easily by simple dispersion at high temperature. By way of example, cetearyl alcohol (and) polysorbate 60 sold under the name Polawax NF by the company Croda and Polawax GP200 sold by the company Croda.

Preferably, one or more "high-HLB nonionic emulsifier"/"low-HLB nonionic emulsifier" pairs will be used as emulsifying system. It may in particular be a nonionic emulsifying system comprising at least one nonionic emulsifier with an HLB of greater than approximately 10 and at least one nonionic emulsifier with an HLB of less than approximately 10.

The ratio of each of the two emulsifiers forming the above-mentioned pair is most commonly determined by calculating the required HLB of the fatty phase used.

By way of preferred emulsifier, mention may be made of:
hydrophilic emulsifiers of the type: PEG 6 stearate and PEG 32 stearate sold under the name Tefose 1500 by Gattefossé; and
lipophilic emulsifiers of the type: PEG-6 isostearate sold under the name Olepal Isostéarique® by Gattefossé.

The composition according to the invention may also comprise a fatty phase.

This fatty phase may comprise, for example, plant oils, mineral oils, animal oils, synthetic oils or silicone oils, and mixtures thereof.

As examples of mineral oils, mention may, for example, be made of liquid paraffins of various viscosities, such as Primol 352®, Marcol 82® and Marcol 152® sold by the company Esso.

As plant oils, mention may be made of sweet almond oil, palm oil, soybean oil, sesame oil, sunflower oil and olive oil.

As animal oils, mention may be made of lanolin, squalene, fish oil with, as a derivative, the perhydrosqualene sold under the name Sophiderm® by the company Sophim.

As synthetic oils, mention may be made of an ester such as cetearyl isononanoate, for instance the product sold under the name Cetiol SN PH® by the company Cognis France, diisopropyl adipate, for instance the product sold under the name Crodamol DA® by the company Croda, isopropyl palmitate, for instance the product sold under the name Crodamol IPP® by the company Croda, and caprylic/capric triglyceride, such as Miglyol 812@ sold by the company Univar.

As silicone oils, mention may be made of a dimethicone, for instance the product sold under the name Q7-9120 Silicone Fluid® with a viscosity of 20 cst to 12 500 cst, by the company Dow Corning, or a cyclomethicone, for instance the product sold under the name ST-Cyclomethicone 5NF®, also by the company Dow Corning.

It will also be possible to use solid fatty substances, such as natural or synthetic waxes, fatty acids, such as stearic acid, fatty alcohols, such as Speziol C18 Pharma, sold by the company Cognis, and texturizing agents of tribehenate type, such as Compritol 888, sold by the company Gattefossé, or hydrogenated castor oils, such as Cutina HR, sold by the company Cognis. In this case, a person skilled in the art will adjust the heating temperature of the preparation according to the presence or absence of these solids.

For the composition according to the invention, oil of the caprylic/capric triglyceride type, such as Miglyol 812®, cetearyl isononanoate such as Cetiol SN PH®, and fatty alcohols such as Speziol C18 Pharma are preferred.

The compositions of the invention may also optionally comprise any additive normally used in the cosmetic or pharmaceutical field, such as surfactants, neutralizing agents of common inorganic or organic acid or base type (by way of example, triethanolamine, 10% sodium hydroxide solution, citric acid/sodium citrate buffer, succinic acid/sodium succinate buffer), sunscreens, antioxidants (butylhydroxyanisole type), fillers, electrolytes, dyes, fragrances, essential oils, cosmetic active agents, moisturizers, vitamins, essential fatty acids, sphingolipids, self-tanning compounds such as DHA, calmatives and skin-protecting agents such as allantoin, or propenetrating agents, or a mixture thereof. Of course, those skilled in the art will take care to select this or these optional additional compound(s), and/or the amount thereof, in such a way that the advantageous properties of the composition according to the invention are not, or are not substantially, adversely affected.

These adjuvants may be present in the composition in a proportion of from 0.0010% to 20% by weight relative to the total weight of the composition.

One subject of the present invention is also the composition as described above, as a medicament.

In particular, the invention relates to the use of a composition as described above for the preparation of a medicament for treating and/or preventing dermatological complaints associated with a keratinization disorder relating to cell differentiation and proliferation, especially for treating acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, acne rosacea, senile acne, solar acne and acne medicamentosa.

Preferably, the invention relates to the use of a composition as described above for the preparation of a medicament for preventing and/or treating acne vulgaris.

Preferably, said compositions according to the invention are administered topically.

In addition, the invention also relates to the cosmetic use of a composition according to the invention, for the treatment of acne-prone skin and for combating the greasy appearance of the skin or the hair.

Another aspect of the invention relates to a process for formulating a complex comprising a naphthoic acid derivative and cyclodextrins and preferably the naphthoic acid derivative is adapalene.

The present invention will now be illustrated by means of the following examples, which cannot limit the scope of the present invention.

DESCRIPTION OF THE FIGURES

FIG. 1: Evaluation of the comedolytic activity of a composition according to the invention and comparison with a formulation containing adapalene dissolved to 0.1% according to application WO 2006/070093
NS: not significant

EXAMPLES

Example 1

Manufacturing Process from the Formation of the Complex until a Preparation Containing the Dissolved Adapalene/Cyclodextrin Complex is Obtained 4 Steps:
Formation of the adapalene/cyclodextrin complex: Phase 1
Formation of the gel: Phase 2
Formation of the complex solution: Phase 3
Completion: Phase 4
Phase 1: Complexing Step
1) Prepare the mixture of powder of
  a. adapalene/RAMEB cyclodextrin (1/n), n being the number of moles of cyclodextrin
  b. Add 10% water
2) Stir
3) Leave to mature for 2 hours at 60° C. and 150 bar
4) Drying phase: 50° C. under vacuum overnight
Phase 2: Formation of the Complex Solution
  1) Weigh and introduce the purified water into the flask
  2) Weigh and introduce the free RAMEB cyclodextrin, maintain stirring until dissolved
  3) Weigh the adapalene/cyclodextrin complex
  4) Introduce the complex into the solution of free RAMEB cyclodextrin
  5) Stir in order to homogenize the mixture
  6) Once homogenized, filter the mixture with a filter having a diameter between 0.2 and 1 µm. The filtration is correct only in the case where the mixture obtained is clear
  7) The complex solution thus obtained should contain 0.2% (w/w) or 0.6% (w/w) of adapalene
Phase 3: Formation of the Formulary Matrix
Step a: Preparation of the Aqueous Phase
Introduced into a beaker, with stirring, if necessary at high temperature, are purified water and the preservative(s), and optionally the gelling agent(s), the chelating agent(s), the hydrophilic emulsifier(s), the stabilizer(s), the humectant(s) and/or emollient(s).
The mixture is brought to approximately 80° C.
Step b:
Introduce into the preceding formulary beaker the excess free RAMEB cyclodextrin, and maintain stirring until dissolved.
Step c (optionally for an emulsion):
Add the necessary amount of complex solution obtained during phase 2 of the present procedure to the preceding aqueous phase (obtained in step b).
Step d (Optionally for Obtaining an Emulsion): Preparation of the Fatty Phase:
Mixing of the lipophilic emulsifiers, oily compounds, solid fatty substances and optionally of the lipophilic emulsifiers and preservatives. The mixture is brought to approximately 75° C.
The mixture is heated and after homogenization the volatile silicone is introduced last, if present in the composition.
Step e (Optional): Emulsification:
At a temperature of 75° C., the fatty phase (step d) is introduced into the aqeuous phase (step c) while stirring in order to carry out the emulsification.
Step f:
Addition of gelling agent (for the preparation of a gel)
The gelling agent(s) are introduced, with stirring, to the phase obtained in b) for the gel. The stirring is maintained until complete homogeneity is achieved.
Step g: Neutralization:
The neutralizing agent for the gelling agent is introduced, if necessary. In the case of a gel it will be introduced into the phase obtained in step f). For an emulsion, it will be introduced into the phase obtained in step e).
Step h: (Optional) Adjustment with Water
If necessary an adjustment with water is carried out.
Step i (for the preparation of a gel containing 0.1% or 0.3% of adapalene): Addition of the complex solution
Phase 4: Completion
After dispersion and neutralization, if necessary, of the gelling agent, add, in equal amounts, the preparation obtained in step h) and the complex solution produced during phase 2. For example, for the preparation of 100 g after dispersion and neutralization, if necessary, of the gelling agent, add, to 50 g of preparation obtained in step h), 50 g of complex solution produced during phase 2 of the present procedure. Stir until homogenized.

This invention enables the formulation of compositions containing 0.1% w/w and 0.3% w/w of adapalene in dissolved form owing to the use of cyclodextrins.

Example 2

2.1. Dissolving the Adapalene/Cyclodextrin Complex

The work was carried out starting from three complexes characterized by 3 different adapalene/cyclodextrin molar ratios, these three ratios were obtained during the manufacture of the complex by SCF:

Complex 1: 1/6
Complex 2: 1/8
Complex 3: 1/10

The table below summarizes the characteristics of these 3 complexes:

TABLE 1

Presentation of the 3 complexes studied

| | Adapalene/ cyclodextrin molar ratio | % of adapalene theoretically present in the complex | % of adapalene present in the complex according to the analytical assays carried out |
|---|---|---|---|
| Complex 1 | 1/6 | 4.8 | 4.709 |
| Complex 2 | 1/8 | 3.1 | 3.832 |
| Complex 3 | 1/10 | 2.8 | 3.082 |

The cyclodextrin present in the complex is RAMEB (Randomly Methylated β-cyclodextrin).

It was sought to dissolve the adapalene/cyclodextrin complexes defined above in purified water.

The adapalene concentrations that it is desired to obtain are 0.2% and 0.6% (w/w) in solution in water. These concentrations were chosen for the purpose of diluting these complex solutions, once stabilized, in a galenic form in order to obtain for example: a gel form containing 0.1 or 0.3% (w/w) of adapalene.

2.2 Procedure for Obtaining a Stable Solution of Adapalene/Cyclodextrin Complex

The first tests for dissolving the complexes show that the mixtures obtained are milky, the whole of the adapalene/cyclodextrin complex introduced into the purified water does not dissolve. This first mixture was filtered in order to obtain a clear solution of adapalene/cyclodextrin complex.

The first stability tests of the complex solutions displayed a rapid decomplexation of the adapalene in purified water.

In order to modify or slow down the decomplexation kinetics, it was chosen to add the free cyclodextrin to the purified water before dissolving the adapalene/cyclodextrin complex.

The procedure used for producing the complex solution is the following:

In a flask, weigh the purified water
Add, if necessary, the free cyclodextrin (Cavasol W7M Pharma)
Magnetically stir the mixture in order to homogenize it
Once the mixture is homogenized, weigh the adapalene/cyclodextrin complex and introduce it into the flask
Stir the mixture for around 2 h in order to homogenize it (there should no longer be any lumps in the flask; the solution is milky)
Once homogenized, filter the mixture through a filter having a diameter between 0.2 and 1 μm. The filtration is correct only in the case where the mixture obtained is clear The complex solution thus obtained should contain 0.2% (w/w) or 0.6% (w/w) of adapalene As mentioned previously, a filtration step is necessary in order to obtain a clear solution of adapalene/cyclodextrin complex.

Once filtered, the complex solutions are assayed in order to determine their exact adapalene titre. This titre makes it possible to determine the loss of adapalene during the filtration step. This test was carried out several times, and the loss of adapalene is reproducible. Knowing the value of the loss of adapalene during the filtration, the exact amount of complex to be incorporated initially during the production of the solution may be determined.

2.3 Chemical Analyses of the Solutions of Adapalene/Cyclodextrin Complexes

Analytical assays were carried out in order to determine the adapalene titre after filtration of the complex solution. This being so as to know the exact amount of complex to be incorporated initially into the purified water as a function of the complex used.

The table below gives the losses of adapalene as a function of the adapalene/cyclodextrin ratio used in the complex:

| adapalene/ M-Beta cyclodextrin complex | Concentration and loss of adapalene | Solution of complex without free cyclodextrin | Solution of complex with free cyclodextrin (80 g/l) |
|---|---|---|---|
| Complex 1 (1/6) | Initial concentration of adapalene (mg/g) | 4.995 | 5.080 |
| | Final concentration of adapalene (mg/g) | 3.935 | 4.008 |
| | Loss of adapalene (%) | 21 | 21 |
| Complex 2 (1/8) | Initial concentration of adapalene (mg/g) | 3.238 | 3.395 |
| | Final concentration of adapalene (mg/g) | 2.910 | 3.140 |
| | Loss of adapalene (%) | 10.1 | 7.5 |
| Complex 3 (1/10) | Initial concentration of adapalene (mg/g) | 4.999 | 5.000 |
| | Final concentration of adapalene (mg/g) | 4.415 | 4.291 |
| | Loss of adapalene (%) | 11.7 | 14.2 |

Conclusion:

the losses of adapalene are reproducible as a function of the complex used and do not appear to depend significantly on the addition or not of free cyclodextrin. For the remainder of the tests, the weight of adapalene/cyclodextrin complex will take into account this loss of adapalene which takes place during the filtration.

In the case of complex 3, the loss of adapalene is around 15%. For this complex, the ratio is 1 to 10. It is therefore possible to estimate the maximum amount of free cyclodextrin in the solution, after filtration, linked to the decomplexation during the solubilization.

At most, around 7 mg/g of cyclodextrin is liberated, there will therefore be at most 87 g/l of free cyclodextrin in the intermediate solution for complex 3 (1/10).

2.4 Physical Stability of the Solutions of Adapalene/Cyclodextrin Complexes

The physical stability of the complex is characterized visually, the systems remain clear as long as the complex is a true complex. As soon as the adapalene is decomplexed, the system becomes cloudy due to the precipitation of the adapalene in the solution studied.

Physical Stability Data of the Complex Solutions:

|  | Stability conditions | |
|---|---|---|
|  | Room temperature (RT) | 4° C. |
| Complex 1 (1/6) + purified water | Presence of crystals of adapalene from $T_{+96\,h}$ | Presence of crystals of adapalene from $T_{+96\,h}$ |
| Complex 1 (1/6) + RAMEB (80 g/l) + purified water | Clear at $T_{+3\,months}$ | Clear at $T_{+3\,months}$ |
| Complex 2 (1/8) + purified water | Presence of crystals of adapalene from $T_{+24\,h}$ | |
| Complex 2 (1/8) + RAMEB (80 g/l) + purified water | Clear at $T_{+2.5\,months}$ | Clear at $T_{+2.5\,months}$ |
| Complex 3 (1/10) + purified water | Clear at $T_{+1.5\,months}$ | Clear at $T_{+1.5\,months}$ |
| Complex 3 (1/10) + RAMEB (80 g/l) + purified water | Clear at $T_{+2.5\,months}$ | Clear at $T_{+2.5\,months}$ |

The adapalene/cyclodextrin complex in solution is stable at 4° C., and room temperature for at least 2.5 months, when free cyclodextrin is present in excess in the solution.

CONCLUSIONS

According to the above results, when the adapalene/cyclodextrin complexes are dissolved in purified water without free cyclodextrin, the stability of the complex is substantially improved in the case where the molar ratio is lowest: Complex 3—1/10 (2.8% adapalene). This solution is stable for at least 2.5 months, irrespective of the temperature conditions applied.

The addition of free cyclodextrin to the water, for the purpose of modifying the decomplexation kinetics of the adapalene/cyclodextrin complex, significantly improves the stability of the dissolved complexes. For complex 1 (1/6: 4.8% adapalene), the solutions are stable for up to 3 months at room temperature compared with the solutions without free cyclodextrin where the same complex is destabilized after 96 h.

To produce gelled formulations containing 0.1 and 0.3% adapalene, it is necessary to take into account the losses of adapalene defined previously, when the complex is being dissolved. The table below presents the adapalene contents of complex solutions used for the remainder of the invention:

| Nature of the complex solution | Stability conditions Room temperature |
|---|---|
| Complex 3 (0.6% adapalene)/RAMEB 100 g/l/purified water | 6.156 mg/g (103) |
| Complex 3 (0.2% adapalene)/RAMEB 100 g/l/purified water | 2.103 mg/g (105) |

2.5 Use of the Formulary Matrix Containing the Dissolved Adapalene/Cyclodextrin Complex The stabilization tests of the cyclodextrin/adapalene complex in solution show that it is necessary to introduce 80 to 100 g/l of free cyclodextrin into the solubilization medium of the complex in order to stabilize it.

The first tests of formulating, in a gel base, solutions of complexes containing free cyclodextrins destabilized the complex.

Indeed, various tests showed that if the gel base does not contain free cyclodextrin, introducing the complex solution into this base results very rapidly in the decomplexation of the adapalene in the formulation.

It is therefore necessary to form a formulary matrix having the same concentration of free cyclodextrin as that used in the complex solution.

Example 3

Process for Manufacturing Gelled Forms

Phase 1: Formation of the Intermediate Complex Solution

1) Weigh and introduce the purified water into the flask
2) Weigh and introduce the free RAMEB cyclodextrin, maintain stirring until dissolved
3) Weigh the adapalene/cyclodextrin complex
4) Introduce the complex into the solution of free RAMEB cyclodextrin
5) Stir in order to homogenize the mixture
6) Once homogenized, filter the mixture with a filter having a diameter between 0.2 and 1 μm. The filtration is correct only in the case where the mixture obtained is clear
7) The intermediate complex solution thus obtained should contain 0.2% (w/w) or 0.6% (w/w) of adapalene Phase 2: Formation of the Gel:

1) In a beaker, weigh the purified water, stir it and heat it to 80° C. using a hotplate.
2) Weigh and introduce the methylparaben
3) Leave stirring until the methylparaben has completely dissolved
4) Leave the solution to cool
5) Weigh and introduce the free RAMEB cyclodextrin, maintain stirring until dissolved
6) Weigh and introduce the propane-1,2-diol, EDTA and phenoxyethanol
7) Homogenize the mixture
8) Weigh and introduce the aqueous gelling agent
9) When the gelling agent is completely dispersed, neutralize with the 10% sodium hydroxide solution (only if the gelling agent is Carbopol 980NF)
10) Leave stirring until homogenized
11) Add qs of water if necessary in order to compensate for the losses of water following evaporation Phase 3: Completion (for a Preparation of 100 g and for Obtaining a Formula Containing 0.1% (w/w) or 0.3% (w/w) of Adapalene)

1) Take a test sample of 50 g of gel (obtained in step 2) and introduce into a beaker
2) Stir at 200 rpm
3) Weigh and introduce into the beaker 50 g of the complex solution produced in step 1
4) Leave stirring until homogenized

Example 4

Formulations Comprising Adapalene at 0.1% and 0.3%

The present invention will now be illustrated by means of the following examples and physical and chemical stability data presented below.

Example 4.1

Adapalene/cyclodextrin Gel Containing 0.1% Adapalene

| Raw materials | Content (% w/w) |
| --- | --- |
| Carbopol 980NF | 1.1 |
| 10% sodium hydroxide solution | 1.6 |
| Complex 1 adapalene/cyclodextrin (1/6) | 2.083 |
| RAMEB | 8.0 |
| Purified water | qs 100 |

Example 4.2

Adapalene/cyclodextrin Gel Containing 0.1% Adapalene

| Raw materials | Content (% w/w) |
| --- | --- |
| Carbopol 980NF | 1.1 |
| 10% sodium hydroxide solution | 1.6 |
| Complex 3 adapalene/cyclodextrin (1/10) | 3.571 |
| RAMEB | 8.0 |
| Purified water | qs 100 |

Example 4.3

Adapalene/cyclodextrin Gel Containing 0.1% Adapalene

| Raw materials | Content (% w/w) |
| --- | --- |
| Carbopol 980NF | 1.1 |
| Propane-1,2-diol | 4.0 |
| EDTA | 0.1 |
| Methylparaben | 0.1 |
| Phenoxyethanol | 0.25 |
| 10% sodium hydroxide solution | 1.6 |
| Complex 3 adapalene/cyclodextrin (1/10) | 3.571 |
| RAMEB | 10.0 |
| Purified water | qs 100% |

Example 4.4

Adapalene/cyclodextrin Gel Containing 0.3% Adapalene

| Raw materials | Content (% w/w) |
| --- | --- |
| Carbopol 980NF | 1.1 |
| Propane-1,2-diol | 4.0 |
| EDTA | 0.1 |
| Methylparaben | 0.1 |
| Phenoxyethanol | 0.25 |
| 10% sodium hydroxide solution | 1.6 |
| Complex 3 adapalene/cyclodextrin (1/10) | 10.714 |
| RAMEB | 10.0 |
| Purified water | qs 100% |

Example 4.5

Adapalene/cyclodextrin Gel Containing 0.3% Adapalene

| Raw materials | Content (% w/w) |
| --- | --- |
| Simulgel 600PHA | 2 |
| Propane-1,2-diol | 2.0 |
| EDTA | 0.1 |
| Sodium docusate | 0.05 |
| Glycerol | 2 |
| Complex 3 adapalene/cyclodextrin (1/10) | 10.714 |
| RAMEB | 10.0 |
| 10% sodium hydroxide solution (w/w) | qs pH 4.5 |
| Purified water | qs 100% |

Example 4.6

Adapalene/cyclodextrin Cream-Gel Containing 0.3% Adapalene

| Raw materials | Content (% w/w) |
| --- | --- |
| Carbopol Ultrez 20 | 0.35 |
| Xanthan gum | 0.1 |
| Caprylic/capric triglycerides | 7 |
| Propane-1,2-diol | 3.0 |
| EDTA | 0.1 |
| Glycerol | 3 |
| Complex 3 adapalene/cyclodextrin (1/10) | 10.714 |
| RAMEB | 10.0 |
| Purified water | qs 100% |

Example 4.7

Adapalene/cyclodextrin Cream-Gel Containing 0.3% Adapalene

| Raw materials | Content (% w/w) |
| --- | --- |
| Carbopol 1382 | 0.35 |
| Hydroxypropyl methyl cellulose | 0.1 |
| Squalane | 4 |
| PEG-6 Isostearate | 1 |
| Cetearyl isononanoate | 4 |
| Propylparaben | 0.05 |
| Lauroglycol | 2.0 |
| EDTA | 0.1 |
| Complex 3 adapalene/cyclodextrin (1/10) | 10.714 |
| RAMEB | 10.0 |
| 10% sodium hydroxide solution (w/w) | qs pH 4.5 |
| Purified water | qs 100% |

Example 4.8

Adapalene/cyclodextrin Lotion Containing 0.3% Adapalene

| Raw materials | Content (% w/w) |
| --- | --- |
| Carbopol ultrez 20 | 0.15 |
| Propylene glycol | 2 |
| HEDTA | 0.1 |
| Methylparaben | 0.1 |
| Stearyl alcohol | 2 |
| Propylparaben | 0.05 |
| PEG-6 stearate/PEG-32 stearate | 2.5 |
| Caprylic/capric triglycerides | 3.5 |
| Complex 3 adapalene/cyclodextrin (1/10) | 10.714 |
| RAMEB | 10.0 |
| 10% sodium hydroxide solution (w/w) | qs pH 4.5 |
| Purified water | qs 100% |

Example 5

Physical Stability of the Formulations

As for the complex solutions presented above, the stability of the adapalene/cyclodextrin complex in the gelled formulations was characterized visually. The clarity of the formulation gives proof of the stability of the complex.

Characterizations at T0:

| T0 | Example 4.3 | Example 4.4 |
| --- | --- | --- |
| Macroscopic appearance | Colorless transparent thick gel | Colorless transparent thick gel |
| Microscopy Zeiss x40 | Absence of crystals Diffuse fluorescence | Absence of crystals Diffuse fluorescence |
| pH | 4.85 | 4.85 |

6 month stability at +4° C., RT and 40° C.

| T 6 months | | Example 4.3 | Example 4.4 |
| --- | --- | --- | --- |
| Macroscopic appearance | | Conforms to T0 at all temperatures | Conforms to T0 at all temperatures |
| Microscopy Zeiss x40 | | Conforms to T0 at all temperatures | Conforms to T0 at all temperatures |
| pH | RT | 5.02 | 5.06 |
| | +4° C. | 5.02 | 5.73 |
| | +40° C. | 4.99 | 5.06 |

Example 6

Chemical Stability of the Formulations

Characterizations at T0:

| T0 | Example 4.3 | Example 4.4 |
| --- | --- | --- |
| Adapalene assay (% of the theoretical titre) | 105 | 101 |

6 month stability at +4° C., RT and 40° C.

| T 6 months | | Example 4.3 | Example 4.4 |
| --- | --- | --- | --- |
| Adapalene assay (% of the theoretical titre) | RT | 102 | 107 |
| | +4° C. | 103 | 106 |
| | +40° C. | 107 | 107 |

The formulations with 0.1 and 0.3% of complexed adapalene, containing free cyclodextrin are physically and chemically stable for at least 6 months at the three temperature conditions tested (+4° C., RT and 40° C.).

Example 6

In Vitro Study of the Release-Penetration Properties of the Preparations of Dissolved Adapalene The composition from Example 4.3 is compared in a release/penetration test known to a person skilled in the art in order to evaluate the amount of active agent that has penetrated.

The experimental results (table below) show that irrespective of the formulation tested, the adapalene is distributed mainly in the skin (epidermis, stratum corneum included, and dermis). The total amounts penetrated are:

| Formulations containing adapalene | | Epidermis (+Stratum corneum) | Dermis | Dose absorbed into the liquid receptor | Total amount penetrated |
|---|---|---|---|---|---|
| Reference: Differin ® Gel | | | | | |
| 0.1% | µg | 0.16 ± 0.04 | 0.01 ± 0.01 | <QL | 0.17 ± 0.05 |
|  | % | 1.77 ± 0.42 | 0.10 ± 0.05 |  | 1.88 ± 0.45 |
| Cyclodextrin gels | | | | | |
| 0.1% adapalene Example 4.3 | µg | 1.28 ± 0.33 | 0.10 ± 0.03 | <QL | 1.38 ± 0.36 |
|  | % | 14.44 ± 3.94 | 1.11 ± 0.33 |  | 15.55 ± 4.22 |

<QL: below the quantification limit

The total amount of adapalene that has penetrated is 1.88% of the dose applied for 0.1% (w/w) Differin® gel and 15.55% of the dose applied for the preparation according to Example 4.3 of the present invention.

These results significantly display a better release and a better penetration, in vitro, on human skin, of the dissolved adapalene according to the present invention, relative to the Differin® gel reference product. The complexed and dissolved adapalene significantly penetrates 8 times more into the skin than the reference product.

Example 7

Evaluation of the Comedolytic Activity of a Composition According to the Invention The composition from Example 4.3 is compared, in a test for measuring the comedolytic activity, with a dispersed adapalene gel (0.1% Differin® gel) and with a preparation containing 0.1% of adapalene dissolved in an aqueous medium with cyclodextrins, described according to Example 1 of application WO 2006/070093 (namely a physical mixture of adapalene and of cyclodextrins without the technology that makes it possible to benefit from the solvating power of a dense fluid under pressure).

Result:

FIG. 1 shows that at the same concentrations of active agent, the composition according to Example 4.3 of the present invention containing dissolved adapalene, displays a greater comedolytic activity than the composition in which adapalene is dissolved and formulated according to Example 1 of application WO 2006/070093. Indeed, the difference observed between Example 1 of application WO 2006/070093 and the Differin® gel placebo is not significant (t-test) whereas a 30% reduction in the number of comedones is noted with the formula prepared according to Example 4.3 of the present invention relative to the placebo.

The invention claimed is:

1. A topical composition comprising, in a physiologically acceptable medium, a soluble molecular complex of adapalene:

and randomly methylated β-cyclodextrin (RAMEB), said soluble molecular complex obtained by technology of dense fluids under pressure, and a stabilizing amount of free RAMEB in water, said composition formulated for topical application.

2. The composition as claimed in claim 1, wherein the dense fluid under pressure is supercritical $CO_2$.

3. The composition as claimed in claim 1, wherein the composition is in the form of a gel.

4. The composition as claimed in claim 1, wherein the concentration of adapalene is between 0.001% and 10% by weight of the total weight of the composition.

5. The composition as claimed in claim 3, wherein the concentration of adapalene is equal to 0.1%.

6. The composition as claimed in claim 4, wherein the concentration of adapalene is equal to 0.3%.

7. A method for treating acne, the method comprising topically applying to the skin of a subject in need of such treatment an effective amount of a composition as claimed in claim 1.

8. A method for treating acne vulgaris, the method comprising topically applying to the skin of a subject in need of such treatment an effective amount of a composition as claimed in claim 1.

9. A cosmetic method for treating acne-prone skin or for combating the greasy appearance of skin or hair, the method comprising topically applying to the skin or hair of a subject in need of such treatment an effective amount of a composition as claimed in claim 1.

10. A process for formulating a composition, wherein the process comprises multiple steps and the resulting composition comprises a soluble molecular complex of adapalene and randomly methylated β-cyclodextrin as claimed in claim 1 wherein the process steps comprise:

Phase 1: Complexing step
1) preparing a mixture of powder of:
a. adapalene and RAMEB cyclodextrin
b. adding 10% water
2) stirring
3) maturing for 2 hours at 60° C. and 150 bar
4) drying at 50° C. under vacuum overnight
to afford a complex of adapalene with RAMEB cyclodextrin Phase 2: Formation of complex solution:
1) weighing and introducing purified water into a flask
2) weighing and introducing free RAMEB cyclodextrin, maintaining stirring until dissolved
3) weighing the adapalene with RAMEB cyclodextrin complex
4) introducing the complex into a solution of free RAMEB cyclodextrin
5) stirring in order to homogenize the mixture
6) once homogenized, filtering the mixture with a filter having a diameter between 0.2 µm and 1 µm, wherein filtration is complete when the mixture obtained is clear
7) and wherein the complex solution thus obtained comprises 0.2% (w/w) or 0.6% (w/w) of adapalene Phase 3: Formation of formulary matrix
Step a: Preparation of aqueous phase
introducing into a beaker, with stirring, if necessary at high temperature, purified water and preservative(s), and optionally gelling agent(s), chelating agent(s), hydrophilic emulsifier(s), stabilizer(s), humectant(s) and/or emollient(s)

bringing the mixture to a temperature of approximately 80° C.

Step b:

introducing into the preceding formulary beaker excess free RAMEB cyclodextrin, and maintaining stirring until dissolved Step c: (optionally for an emulsion):

adding an amount of complex solution obtained in phase 2 to the preceding aqueous phase (obtained in step b)

Step d (optionally for obtaining an emulsion): Preparation of fatty phase:

mixing of lipophilic emulsifiers, oily compounds, solid fatty substances and optionally the lipophilic emulsifiers and preservatives, and bringing the mixture to a temperature of approximately 75° C.

heating the mixture and after homogenization introducing a volatile silicone, if present in the composition Step e (optional): Emulsification:

at a temperature of 75° C., introducing the fatty phase (step d) into the aqeuous phase (step c) while stirring in order to carry out the emulsification Step f: Addition of gelling agent (for preparation of a gel)

introducing gelling agent(s), with stirring, to the phase obtained in b) for the gel, maintaining stirring until complete homogeneity is achieved Step g: Neutralization:

introducing neutralizing agent for the gelling agent, if necessary, and in the case of a gel, introducing the neutralizing agent into the phase obtained in step f) and in the case of an emulsion, introducing the neutralizer into the phase obtained in step e)

Step h: (optional) adjustment with water if necessary, adjusting with water

Step i (for preparation of a gel comprising 0.1% or 0.3% adapalene:

Addition of complex solution

Phase 4: Completion after dispersion and neutralization, if necessary, of the gelling agent, adding, in equal amounts, the preparation obtained in step h) and the complex solution produced during phase 2 and stirring until homogenized.

11. The composition as claimed in claim 4, wherein the concentration of adapalene is between 0.01% and 5% by weight of the total weight of the composition.

12. The composition as claimed in claim 4, wherein the concentration of adapalene is between 0.05% and 2% by weight of the total weight of the composition.

13. The method as claimed in claim 7, wherein the acne is acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, senile acne, solar acne or acne medicamentosa.

14. The process as claimed in claim 10, wherein the complex of adapalene with randomly methylated β-cyclodextrin (RAMEB) has a 1/10 molar ratio of adapalene to RAMEB.

15. A topical composition comprising, in a physiologically acceptable medium which comprises water, (a) a water-soluble molecular complex of adapalene with randomly methylated β-cyclodextrin (RAMEB) having a 1/10 molar ratio of adapalene to RAMEB; (b) a stabilizing amount of free RAMEB; and (c) one or more gelling agents; formulated as a topical gel having a final concentration of adapalene of 0.1% or 0.3% by weight in dissolved form.

16. The composition according to claim 15, wherein the stabilizing amount of free RAMEB is from about 8% to about 10% by weight of the total composition.

* * * * *